United States Patent
Starch

[11] Patent Number: 5,888,492
[45] Date of Patent: *Mar. 30, 1999

[54] RINSE-OFF SKIN CONDITIONER

[75] Inventor: Mike Starch, Cincinnati, Ohio

[73] Assignee: The Andrew Jergens Company, Cincinnati, Ohio

[ * ] Notice: The term of this patent shall not extend beyond the expiration date of Pat. No. 5,578,299.

[21] Appl. No.: 861,108

[22] Filed: May 21, 1997

[51] Int. Cl.$^6$ .............................. A61K 31/74; A61K 7/50
[52] U.S. Cl. .................. 424/78.03; 424/70.19; 424/70.31; 424/70.21; 510/159
[58] Field of Search .............. 424/70.11, 78.03, 424/70.21, 70.19; 510/159

[56] References Cited

U.S. PATENT DOCUMENTS

| | | | |
|---|---|---|---|
| 5,120,532 | 6/1992 | Wells et al. | 424/70 |
| 5,143,723 | 9/1992 | Calvo | 424/63 |
| 5,221,534 | 6/1993 | DesLauriers | 424/78.03 |
| 5,558,872 | 9/1996 | Jones et al. | 424/78.03 |
| 5,578,299 | 11/1996 | Starch | 424/78.03 |

*Primary Examiner*—Sally Gardner-Lane
*Attorney, Agent, or Firm*—Oblon, Spivak, McClelland, Maier & Neustadt, P.C.

[57] ABSTRACT

A rinse-off skin conditioning composition employs a hydrocarbon oil, a di-block or tri-block copolymer as a viscosity improver, optionally a fatty acid ester as an emollient, and a surfactant soluble in the mixture of the hydrocarbon oil, a copolymer and fatty acid ester, and capable of dispersing said composition in water. The composition may be applied when showering and then rinsed away, leaving a residue of approximately 3–25 percent by weight of the total applied after rinsing. The residue has a skin-conditioning effect.

9 Claims, No Drawings

RINSE-OFF SKIN CONDITIONER

BACKGROUND OF THE INVENTION

1. Field of the Invention

This invention pertains to a skin-conditioning composition which is designed to be applied and rinsed off. More specifically, the inventive composition is intended for use in the shower, to be applied to wet human skin (that is, skin with water on it), and subsequently rinsed away, leaving a skin-conditioning deposit on the skin's surface which is aesthetically acceptable.

2. Background of the Invention

Various skin-conditioning compositions exist which are intended to be introduced to bath water, and act to soften or otherwise condition the skin while bathing. The typical skin-conditioning agent is a mineral oil or oils, and in bathing compositions, are of relatively low viscosity, for dispersion in the water. Additionally, polymers are known agents for combining with mineral oils in skin softening compositions, per se.

Other cosmetic compositions particularly designed for skin conditioning include those discussed in U.S. Pat. No. 5,152,991, which is directed to cosmetic compositions containing selectively hydrogenated styrene/butadiene copolymers. These copolymers are specifically designed to prevent removal of the composition in which they are formulated from the skin, or at least to prevent easy washing off of the cosmetic formulation. The copolymers described are random, and the compositions contain at least 40 percent by weight water.

U.S. Pat. No. 5,143,723 is directed to colored cosmetic compositions, or "make-up", such as lipstick, nail coloring and the like. The compositions addressed are intended to exhibit particular brilliance of color, by incorporating a solvated dye into the resins, including styrene block polymers or butene/ethylene copolymers.

An additional cosmetic composition which employs particulate polymers, rather than a polymer matrix, is addressed in European Patent Application 497,144, that requires particulate styrene/ethylene/propylene copolymer components, as well as conventional emollients and agents such as colorants, UV blockers and the like.

A different type of cosmetic composition is addressed in U.S. Pat. No. 5,221,534, DesLauriers et al, the entirety of which is incorporated herein by reference. This reference is directed to compositions employing gelled mineral oil with blends of di-block and tri-block copolymers based on synthetic thermoplastic resins. In general, the compositions contain 80–99 percent by weight of an oil, and 1–20 percent by weight of a copolymer which includes one of either a di-block or tri-block copolymer which consist of a hard segment, such as styrenic and a soft segment such as butadiene. Thus, tri-block copolymers of styrene/butadiene/styrene and styrene/isoprene/styrene are employed, as well as di-block, copolymers such as a styrene/ethylene propylene, styrene/ethylene butadiene are employed to gel the oil, imparting a substantially different viscosity. The gel is designed as a carrier for various agents for topical administration. Surfactants are not required for the composition.

None of the art discussed, and cosmetics available, provide an adequate composition for use in the shower. Specifically, the composition needs a heightened viscosity so that it can be easily applied to wet human skin, and yet excess beyond that necessary to condition the skin may be rinsed off easily, while leaving a conditioning residue behind for skin softening effectiveness. In general, an oily residue of up to 25 percent by weight, of the composition, can be aesthetically tolerated. Moreover, a gelled material, per se, provides an undesirable feel, and is aesthetically unpleasant for application in the shower. Accordingly, a lotion composition is preferred and the object of continuing research in the cosmetic industry.

U.S. Pat. No. 5,578,299, Starch, describes a composition similar to that of the present application. It is not prior art. This patent is incorporated in its entirety herein by reference.

SUMMARY OF THE INVENTION

Applicant has developed a rinse-off skin-conditioning composition for use in the shower, or under other conditions where the skin is wet but not immersed in water, which is easily rinsed off with water, by showering, to leave a residue of skin-conditioning material on the surface of the skin to which it is applied, without depositing too much material and in an aesthetically acceptable vehicle. The composition comprises (a) a hydrocarbon oil, particularly selected as a skin-conditioning agent, which may be a straight chain hydrocarbon of 10–40 carbon atoms, such as mineral oils, or a branched chain hydrocarbon of about 10–200 carbon atoms, as known to those of skill in the art. The second element (b) is a copolymer which is a di-block copolymer, tri-block copolymer or mixture thereof to increase oil viscosity. These copolymers, described in U.S. Pat. No. 5,221,534, are comprised of a hard segment of styrene units and a soft segment such as butadiene and isoprene. The third element (c) is an optional element, a fatty acid ester which is generally a fatty acid ester of straight or branched chain organic acids and monohydric or polyhydric alcohols. The remaining essential element (d) of the composition is a surfactant which must be soluble in the hydrocarbon oil, the copolymer/oil gel, and the fatty acid ester as well as being effective in dispersing that combination into water. Thus, the surfactant presence is necessary to ensure that the product substantially washes off. At the same time, if effectively 100 percent of the product is rinsed away, little or no skin-conditioning effect will be attained. Amounts substantially in excess of 25 percent by weight of the formula, as applied, are aesthetically-undesirable to users. Amounts substantially below about 3 percent provide no perceptible effect, and thus, the surfactant is selected so as to leave about 3–25 percent of the formula deposited on the skin after rinsing away.

DETAILED DESCRIPTION OF THE INVENTION

The inventive composition is intended to provide skin-conditioning effects, particularly skin hydrating and softening effects. To this end, skin softening and/or water occlusive oils are employed, as is conventional in other cosmetic preparations which are not designed as rinse-off formulations. Additionally emollient properties can be provided by the fatty acid ester, where desired. In contrast to cream compositions, or bath additives, the invention addressed herein must have the requisite viscosity to permit application in the shower, or under conditions where the skin is wet but not immersed in water, and at the same time be susceptible of being easily rinsed away. Thus, after completion of showering, the individual using the product should be able to retain the skin-conditioning effect, without an oily or aesthetically unpleasant effect due to excessive deposit of the material remaining on the skin after showering. Thus, physico-chemical characteristics including viscosity, water dispersibility, hydrating potential and the like must be balanced in one composition. It will therefore be appreciated that the invention is characterized by the combination and balancing of many elements. Nonetheless, the elements can be considered separately, as is discussed below.

Hydrocarbon Oil

The principal softening agent and vehicle for the composition of this agent is a hydrocarbon oil. The oil may be natural or synthetic. Examples include straight chain hydrocarbons of about 10–40 carbon atoms, generally referred to as mineral oils. Branched chain hydrocarbons, having from about 10 to as many as 200 carbon atoms may also be used, depending on adjustments made in the remaining components for desired viscosity. Among branched chain hydrocarbons of this type that may be considered are polydecenes, polyisobutenes, hydrogenated polyisobutenes, squalane and squalene. Mixtures of these oils can of course be used. Natural mineral oil is generally preferred.

The oil is a skin-conditioning agent, and accordingly, must be contained in sufficient quantities such that a residue of the oil is deposited after rinsing, to effect skin conditioning. In general, the oil is present in amounts of about 49–98 percent by weight mineral oil.

Copolymers

Conventional bath oil and skin conditioning body lotions employ high amounts of mineral oil. Such formulations tend to have a low viscosity, such that, if applied when showering or to wet skin, the oil will literally "run off" the body as it is applied. This will preclude achieving any skin-conditioning effects. Increasing the viscosity of these types of hydrocarbon oils in a composition suitable for topical application is however quite difficult. There are relatively few technologies available to thicken non-polar oil systems such as mineral oil. While specialized thickeners can be used, these are expensive and difficult to work with. They are principally useful in the preparation of pastes or gels, but are not easily susceptible of use in the preparation of a pourable lotion.

U.S. Pat. No. 5,221,534 is directed to mineral oil gels wherein the mineral oil, including mineral oil suitable for use in the invention claimed below, are "gelled" by the addition of di-block and/or tri-block copolymers comprised of styrenic monomers and low glass transition temperature (Tg) monomers, such as butadiene and isoprene. While the amount of polymer employed in U.S. Pat. No. 5,221,534 per unit of oil, on a weight basis, is greater than that employed herein, because of the different viscosity requirements identified, the same copolymers can be employed in the claimed invention. Suitable di-block and tri-block polymers are those commercially available from Shell Chemical Company as the KRATON®D and KRATON®G product lines. Particularly preferred are the KRATON®G 1650, a styrene/ethylene-butylene/styrene tri-block copolymer, and KRATON®G 1702, an ethylene-propylene/styrene di-block copolymer. While either di-block or tri-block copolymers of this type may be used, a preferred composition uses a blend of di-block and tri-block copolymers in a weight ratio of 2:1 to 1:3.

The term "styrenic" in the context of the present application denotes styrene as well as substituted styrene such as ortho-, meta-l and pure-alkyl styrene, and x-alkyl-styrene where alkyl denotes a $C_1$–$C_3$ alkyl group. An unexpected result obtained from combining the copolymer with the mineral oil in the present invention is a sharply improved skin-conditioning effect, as compared with the use of hydrocarbon oil formulas in non-rinse-off environments. Thus, the addition of the polymer not only improves viscosity performance, such that the product can be applied in the shower, without running off, but, after rinsing, skin-conditioning effects are improved. As a percentage by weight, of the entire composition, the copolymer is present in amounts of 0.5–5 percent by weight, in contrast with the hydrocarbon oil of 49–98 percent by weight.

It should be noted that an alternative approach embraced within the claimed invention is to prepare the composition by utilizing a mineral oil gel of the type embraced by U.S. Pat. No. 5,221,534, and adding additional mineral oil thereto. A suitable, commercially available gel for this type of approach are GEAHLENE gels available from Penreco, a division of Pennzoil Products Company. An exemplary commercially available gel is GEAHLENE 500 which is a mixture of mineral oil, polystyrene-poly(ethylene/butylene)-polystyrene triblock copolymer and poly(ethylene/propylene)-polystyrene diblock copolymer of which approximately 7 percent by weight is copolymer. In the situation where a mineral oil gel is used as the starting point, and mineral oil is added thereto, the gel constitutes, on a weight basis, 20–50 percent of the entire composition, and the added oil constitutes 4–89 percent of the entire composition.

While technically accurate, the description of a "gel" diluted by an "oil" is chemically inaccurate. The claimed invention employs the di-block/tri-block copolymers employed in GEAHLENE gel compositions for the same reason disclosed in U.S. Pat. No. 5,221,534, to enhance viscosity, but the claimed composition is not correctly identified as a gel. Indeed gels, as described in that patent, would be aesthetically unacceptable as a rinse-off product for shower application.

Emollients

As an emollient additive to the inventive composition, one or more of a fatty acid ester, branched chain fatty alcohol or acid, or silicones may be incorporated with the hydrocarbon oil and copolymer. As the emollient properties contributed are optional and not required for skin-conditioning effects, this element is optional, and can be included, on a weight basis, at 0–40 percent of the composition as a whole. The emollient can also be used to modify the "feel" or aesthetics of the deposit on the skin. The emollient(s) must be liquid at room temperature, or form a liquid preparation when added to the mineral oil and copolymer. Composition blending is facilitated by selecting an emollient(s) which is liquid at room temperature.

There are a wide variety of fatty acids esters which meet the described requirements. Accordingly, suitable esters will be selected, in appropriate weight amounts, to stay within aesthetically acceptable limits. Throughout this document, reference is made to "fatty" carbon-based compounds and compositions, such as fatty acids and fatty alcohols. This term is intended to refer to substantially water-insoluble compounds.

Suitable fatty acid esters include fatty acids of monohydric alcohols of the general formula $R_1$—O—CO—$R_2$, wherein $R_1$ and $R_2$ are hydrocarbon chains derived from animal and/or vegetable fats and oils, or petroleums. Suitable examples include isopropyl palmitate, isopropyl myristate, isopropyl isostearate, octyl isononanoate, isocetyl stearate, oleyl oleate, isohexyl neopentanoate, myristyl neopentanoate, myristyl propionate, decyl oleate, cetearyl octanoate, octyl palmitate, isodecyl oleate, octyl hydroxystearate, cetyl octanoate, and isostearyl isostearate, wherein octyl and octonoate moieties may be straight chain or branched, such as 2-ethylhexyl.

Fatty esters of ethoxylated monohydric alcohols of the general formula $R_1$—O—$(CH_2CH_2O)_x$—CO—$R_2$, wherein $R_1$ and $R_2$ are defined as above, and x is 1–30, may also be employed. Suitable examples include myreth-3 laurate, laureth-2 octanoate (straight or branched), myreth-3 myristate and myreth-3 palmitate.

Instead of simple esters, di- and tri-esters of monohydric alcohols of the type described above, that is, esters of fatty alcohols and polycarboxylic acids may be employed. Examples include diisopropyl adipate, diisostearyl fumarate, triisostearyl trilinoleate, diisopropyl sebacate, diisostearyl dilinoleate, trioctyl citrate (straight or branched), diisopropyl dilinoleate, and triisostearyl citrate.

In the alternative, rather than using polycarboxylic acids, polyhydric alcohols may be employed in the preparation of fatty esters for use as the ester component of this invention. Examples include propylene glycol dipelargonate, glyceryl isostearate, neopentyl glycol dicaprate, trioctanoin (glyceryl trioctanoate), triolein, propylene glycol laurate, neopentyl glycol dioctanoate, neopentyl glycol dilaurate, and triisostearin (glyceryl triisostearate) wherein octanoate moieties may be straight or branched.

Of course, related esters comprised of selections from the fatty acids and alcohols identified, as well as mixtures of the fatty esters identified, may be employed.

Instead of, or in addition to, the esters described above, branched chain fatty alcohols or acids liquid at room temperature may be used, if soluble in the hydrocarbon oil component. Representative members of this class include isostearic acid, butyl octanoic acid, hexyl decanoic acid, octyl dodecanoic acid, decyl dodecanoic acid, butyl octanol, hexyl decanol, octyl dodecanol and decyl dodecanol.

A different class of emollients which may be used in place of the esters, acids and alcohols described above, or together therewith, is synthetic liquid silicone polymers having a monomer general structure.

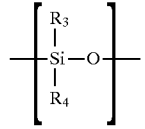

wherein $R_3$ and $R_4$ are lower alkyl of 1–6 carbon atoms. Examples of suitable liquid silicone polymers include dimethicone, dimethiconol and cyclomethione.

Surfactant

The addition of a surfactant is a required element for the rinse-off skin conditioner of the claimed invention. Thus, the surfactant must be both soluble in the combination of the hydrocarbon oil, copolymer and ester, and simultaneously be effective in dispersing the formula into water, that is, to achieve effective rinsing off. A simple test to determine the suitability of any surfactant for the claimed invention is to add the surfactant to the composition and shake it together with an equal or greater amount of water. When an appropriate surfactant is selected, a white, milky emulsion is produced. Suitable surfactants include nonionic and anionic surfactants.

Generically, classes of acceptable surfactants can be identified. It must be noted, however, that both the shaking test described above, and the skin deposition test described below, must be satisfied by acceptable surfactants. The following classes of surfactants are preferred:

1) Ethoxylated Long Chain (fatty) Alcohols, of the formula

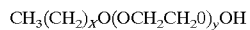

where x is an integer of about 8–22 and y is an integer of about 2–6. Unsaturated variants (e.g. Oleth-3) may also be employed.

2) Ethoxylated Sorbitan Esters

Examples include various polysorbate/polyethylene glycol sorbitan ester surfactants.

3) Sodium Dialkyl Sulfosuccinates
wherein the alkyl groups are from 6–16 carbon atoms.

4) Partial Phosphoric Acid Esters of Ethoxylated Long Chain (fatty) Alcohols of the formula

where x is an integer of about 8–22 and y is an integer from about 2–6.

5) Monoethanol Amides of Long Chain (fatty) Alcohols of the formula

where x is an integer of about 8–22.

6) Acetic Acid Esters of Ethoxylated Propylene Glycol Ethers of Long Chain (fatty) Alcohols.

Specific surfactants within these classes have been identified as useful.

Among the nonionic surfactants, Laureth-3, Laureth-4, Oleth-3, Isosteareth-2, Trideceth-3, as well as C9-11 Pareth-3, C11-15 Pareth-3, C12-13 Pareth-3, C11-15 Pareth-5, PEG-40 Sorbitan Peroleate, PEG-40 Sorbitan Hexaoleate, PEG-50 Sorbitan Hexaoleate, Steareth-2, cocamide MEA, lauramide MEA, mystiramide MEA and Polysorbate-21 surfactants have been identified as suitable.

Anionic surfactants include dioctyl (straight or branched chain) sodium sulfosuccinate, dihexyl sodium sulfosuccinate, ditridecyl sodium sulfosuccinate, laureth-3 phosphate, propylene glycol isocetheth-3 acetate, sodium dinonyl sulfosuccinate, propylene glycol isoceteth-3 acetate and propylene glycol ceteth-3 acetate can be identified. The suitable surfactant may include a mixture of the surfactants, including a mixture of anionic with non-ionic surfactants.

The composition is sensitive to the amount of surfactant incorporated. If too little surfactant is incorporated, too high a percentage of the composition is left on the skin after rinsing or rinsing becomes quite difficult. A minimum amount of surfactant is about 1 percent by weight, of the total composition. Similarly, if higher amounts of surfactant than appropriate are included, the composition is effectively completely rinsed from the body, and little or no skin-conditioning effect is obtained. In general, a desirable percentage of the formulation left as a residue on the skin after rinsing is about 3–25 percent by weight. Preferred amounts include 6–15 percent by weight. Accordingly, depending on the surfactant selected, a range of 1–6, preferably 1–3, and more preferably 2–3 percent by weight of the total composition is suitable. At a reduced surfactant concentration the potential for skin irritation is reduced, thus, low concentration of surfactant is preferred.

Additional Elements

Conventional cosmetic additives may be added to the rinse-off skin conditioner claimed herein. Principle amongst these are fragrances, antioxidants, preservatives and pigments or colorants. Additional active agents, such as antibiotics, including bacteriostats and anti-fungal agents, may be incorporated if complimentary to the composition. Specifically, these additional additives will be incorporated in limited weight amounts selected so as not to interfere with the viscosity, "feel" and rinse-off characteristics of the base composition. Such additives are conventional to those of skill in the art.

The composition is prepared by simple blending of the various formulation components, pursuant to art-recognized technology. Certain copolymers may require limited heating for thorough blending, as discussed in the U.S. Pat. No. 5,221,534. Under the current state of the law, the method of preparation, per se, of the inventive composition does not constitute an aspect of the invention.

EXAMPLES

To demonstrate the effective weight range for the mineral oil, copolymer, surfactant and fatty ester acceptable in the claimed composition, examples were prepared by combining a mineral oil gel such as that described in U.S. Pat. No. 5,221,534, specifically GEAHLENE 500, with additional mineral oil, a surfactant and a fatty ester. The GEAHLENE 500 is a mixture of mineral oil, polystyrene-poly(ethylene/butylene)-polystyrene triblock copolymer and poly(ethylene/propylene)-polystyrene diblock copolymer of which approximately 7 percent is copolymer. The fatty ester selected was octyl (branched chain) isononanoate and the surfactant selected was Laureth-3.

The compositions were prepared by conventional blending and evaluated with respect to the amount of residue left after rinsing. The test involves the application of the composition to a hydrated plastic film. The film is then rinsed under running water, dried and weighed to determine how much residue is deposited. This test simulates the application conditions of the composition onto human skin in the shower. Actual human testing demonstrates that the standardized experiment correlates with the experience of those who used formulas of differing compositions under experimental conditions. Beyond the residue test, the compositions were measured to determine viscosity. The results are reflected in Table 1 hereto. Further, different surfactants were tested in the above formulation and the residue was measured. The results are presented in Table 2 below. In addition, formulations with mixed surfactants with total surfactant levels ranging from 1.0 to 1.50 are presented in Table 3. The above formulations include single surfactant as well as mixtures of surfactants.

Compositions were also tested to determine the potential for skin irritative subjects wore closed patches (Hilltop Chamber) for 48 hours. Erythera was measured 3 hours after patch removal. The results are shown in Table 4.

TABLE 1

FORMULA COMPONENTS
GEAHLENE

| Trial No. | Ester | Surfactant | 500 | Mineral Oil | Viscosity | Residue* |
|---|---|---|---|---|---|---|
| 1 | 40.00% | 0.00% | 50.00% | 10.00% | 2112 | 92.1 |
| 2 | 40.00% | 0.00% | 10.00% | 50.00% | 33 | 83.6 |
| 3 | 0.00% | 0.00% | 50.00% | 50.00% | 4113 | 96 |
| 4 | 20.00% | 0.00% | 30.00% | 50.00% | 750 | 94.6 |
| 5 | 20.00% | 0.00% | 10.00% | 70.00% | 48 | 85.9 |
| 6 | 0.00% | 0.00% | 10.00% | 90.00% | 68.95% | 88.7 |
| 7 | 40.00% | 3.00% | 30.00% | 27.00% | 346 | 6.2 |
| 8 | 0.00% | 0.50% | 30.00% | 69.50% | 1085 | 60.1 |
| 9 | 20.00% | 0.50% | 30.00% | 49.50% | 712 | 47.4 |
| 10 | 0.00% | 2.00% | 30.00% | 68.00% | 1082 | 8.6 |
| 11 | 20.00% | 2.00% | 30.00% | 48.00% | 632 | 8.5 |
| 12 | 0.00% | 3.00% | 30.00% | 47.00% | 577 | 3.8 |
| 13 | 20.00% | 3.00% | 30.00% | 67.00% | 1028 | 4.9 |
| 14 | 20.00% | 3.00% | 50.00% | 27.00% | 2870 | 5.3 |
| 15 | 0.00% | 3.00% | 10.00% | 87.00% | 65 | 3.5 |
| 16 | 40.00% | 6.00% | 50.00% | 4.00% | 1620 | 6.5 |
| 17 | 40.00% | 6.00% | 10.00% | 44.00% | 30.4 | 1.05 |
| 18 | 0.00% | 6.00% | 50.00% | 44.00% | 3902.5 | 4.6 |
| 19 | 20.00% | 6.00% | 10.00% | 64.00% | 45 | 3.1 |
| 20 | 0.00% | 6.00% | 30.00% | 64.00% | 871.5 | 2.5 |
| 21 | 0.00% | 6.00% | 10.00% | 84.00% | 63.5 | 1.8 |

*weight percent of formula left after rinsing

TABLE 2

Compositions with Single Surfactants

|  | K | L | M | N | P | Q | R | S | T |
|---|---|---|---|---|---|---|---|---|---|
| GEAHLENE 500 | 30.14 | 30.54 | 30.93 | 30.14 | 30.93 | 30.14 | 30.93 | 30.14 | 30.54 |
| MINERAL OIL | 46.36 | 46.97 | 41.57 | 46.36 | 47.57 | 46.36 | 47.57 | 46.36 | 46.97 |
| OCTYL ISONONANOATE | 20.00 | 20.00 | 20.00 | 20.00 | 20.00 | 20.00 | 20.00 | 20.00 | 20.00 |
| Isosteareth-2 | 3.50 | 2.50 | 1.50 | | | | | | |
| Oleth-3 | | | | 3.50 | 1.50 | | | | |
| Trideceth-3 | | | | | | 3.50 | 1.50 | | |
| C11–15 Pareth-3 | | | | | | | | 3.50 | 2.50 |
| Laureth-3 | | | | | | | | | |
| C9–11 Pareth-3 | | | | | | | | | |
| Laureth-4 | | | | | | | | | |
| C11–15 Pareth-5 | | | | | | | | | |
| C9–11 Pareth-6 | | | | | | | | | |
|  | 100.00 | 100.00 | 100.00 | 100.00 | 100.00 | 100.00 | 100.00 | 100.00 | 100.00 |
| TOTAL SURFACTANT --> | 3.50 | 2.50 | 1.50 | 3.50 | 1.50 | 3.50 | 1.50 | 3.50 | 2.50 |
| % RESIDUE --> | 8.6 | 11.0 | 40.7 | 9.1 | 26.8 | 2.3 | 15.3 | 13.8 | 12.1 |

TABLE 2-continued

Compositions with Single Surfactants

|  | U | V | W | X | Y | Z | AA | BB | CC |
|---|---|---|---|---|---|---|---|---|---|
| GEAHLENE 500 | 30.93 | 31.13 | 30.93 | 30.93 | 30.14 | 29.94 | 30.93 | 30.14 | 30.93 |
| MINERAL OIL | 47.57 | 47.87 | 47.57 | 47.57 | 46.36 | 46.06 | 47.57 | 46.36 | 47.57 |
| OCTYL ISONONANOATE | 20.00 | 20.00 | 20.00 | 20.00 | 20.00 | 20.00 | 20.00 | 20.00 | 20.00 |
| Isosteareth-2 | | | | | | | | | |
| Oleth-3 | | | | | | | | | |
| Tridecath-3 | | | | | | | | | |
| C11–15 Pareth-3 | 1.50 | | | | | | | | |
| Laureth-3 | | 1.00 | 1.50 | | | | | | |
| C9–11 Pareth-3 | | | | 1.50 | 3.50 | 4.00 | | | |
| Laureth-4 | | | | | | | 1.50 | 3.50 | |
| C11–15 Pareth-5 | | | | | | | | | 1.50 |
| C9–11 Pareth-6 | | | | | | | | | |
|  | 100.00 | 100.00 | 100.00 | 100.00 | 100.00 | 100.00 | 100.00 | 100.00 | 100.00 |
| TOTAL SURFACTANT --> | 1.50 | 1.00 | 1.50 | 1.50 | 3.50 | 4.00 | 1.50 | 3.50 | 1.50 |
| % RESIDUE --> | 36.7 | 36.1 | 10.6 | 26.0 | 7.9 | 10.7 | 12.7 | 8.5 | 18.0 |

|  | DD | EE | FF | GG | HH | JJ | KK | LL | MM | NN | PP |
|---|---|---|---|---|---|---|---|---|---|---|---|
| GEAHLENE 500 | 30.14 | 30.93 | 30.14 | 30.93 | 30.14 | 31.13 | 30.93 | 30.04 | 29.96 | 31.01 | 30.00 |
| MINERAL OIL | 46.36 | 47.57 | 46.36 | 47.57 | 46.36 | 47.87 | 47.57 | 46.21 | 46.09 | 47.69 | 46.15 |
| OCTYL ISONONANOATE | 20.00 | 20.00 | 20.00 | 20.00 | 20.00 | 20.00 | 20.00 | 19.85 | 19.85 | 19.85 | 20.00 |
| FRAGANCE | | | | | | | | 0.50 | 0.45 | 0.45 | 0.45 |
| PHOSPHORIC ACID | | | | | | | | | 0.05 | | |
| C12–13 Pareth-3 | | | | 1.50 | 3.50 | | | | | | |
| PEG-40 Sorbitan Peroleate | | | | | | 1.00 | 1.50 | | | | |
| Steareth-2 | | | | | | | | 3.40 | | | |
| Polysorbate-21 | | | | | | | | | 3.60 | | |
| Laureth-3 Phosphate | | | | | | | | | | 1.00 | 3.40 |
| C11–15 Pareth-5 | 3.50 | | | | | | | | | | |
| C9–11 Pareth-6 | | 1.50 | 3.50 | | | | | | | | |
|  | 100.00 | 100.00 | 100.00 | 100.00 | 100.00 | 100.00 | 100.00 | 100.00 | 100.00 | 100.00 | 100.00 |
| TOTAL SURFACTANT --> | 3.50 | 1.50 | 3.50 | 1.50 | 3.50 | 1.00 | 1.50 | 3.40 | 3.60 | 1.00 | 3.40 |
| % RESIDUE --> | 4.5 | 35.9 | 33.8 | 12.3 | 6.3 | 17.5 | 6.7 | 5.5 | 9.3 | 20.0 | 1.8 |

TABLE 3

Composition with Mixed Surfactants (Concentrations < = 1.5%)

|  | A | B | C | D | E | F | G | I | H | J |
|---|---|---|---|---|---|---|---|---|---|---|
| GEAHLENE 500 | 31.13 | 31.05 | 31.05 | 31.13 | 30.93 | 30.93 | 34.61 | 30.73 | 27.74 | 30.93 |
| MINERAL OIL | 47.81 | 41.75 | 47.15 | 47.81 | 41.57 | 41.57 | 53.33 | 47.21 | 60.26 | 47.57 |
| OCTYL ISONONANOATE | 20.00 | 20.00 | 20.00 | 20.00 | 20.00 | 20.00 | 10.00 | 20.00 |  | 20.00 |
| PEGA DIHEPTANOATE | | | | | | | | | 10.00 | |
| FRAGRANCE | | | | | | | 0.48 | 0.48 | 0.48 | |
| PHOSPHORIC ACID | | | | | | | 0.02 | 0.02 | 0.02 | |
| Laureth-3 | | | | | 1.00 | 0.50 | 1.35 | 1.00 | 1.35 | |
| Oleth-3 | | | | 0.40 | 0.50 | | | | | |
| Trideceth-3 | 0.25 | | | | 0.50 | | | | | |
| C9–11 Pareth-3 | | 0.40 | | | | | | | | |
| Polysorbate-21 | | | | | | | 0.15 | 0.50 | 0.15 | |
| PEG 40 Soibitan Peroleate | 0.75 | 0.80 | 0.80 | | 0.50 | 1.00 | | | | 1.00 |
| Propylene Glycol Isoceteth-3 Acetate | | | | | | | | | | 1.50 |
|  | 100.00 | 100.00 | 100.00 | 100.00 | 100.00 | 100.00 | 100.00 | 100.00 | 100.00 | 100.00 |
| TOTAL SURFACTANT --> | 1.00 | 1.20 | 1.20 | 1.00 | 1.50 | 1.50 | 1.50 | 1.50 | 1.50 | 1.50 |
| % RESIDUE --> | 18.8 | 16.9 | 13.6 | 33.9 | 18.3 | 11.4 | 9.2 | 13.8 | 12.1 | 9.7 |

TABLE 4

Compositions Prepared for Patch Test (Skin Irritation)

|  | 1 | 2 | 3 | 4 | 5 | 6 |
|---|---|---|---|---|---|---|
| GEAHLENE 500 | 28.19 | 30.04 | 27.88 | 27.72 | 27.56 | 30.73 |
| MINERAL OIL | 61.31 | 46.21 | 60.62 | 60.28 | 59.94 | 47.27 |
| OCTYL ISO-NONANOATE | | 19.85 | | | | 20.00 |
| PEGA DIHEP-TANOATE | 10.00 | | 10.00 | 10.00 | 10.00 | |
| FRAGRANCE | 0.48 | 0.48 | 0.48 | 0.48 | 0.48 | 0.48 |
| PHOSPHORIC | 0.02 | 0.02 | 0.02 | 0.02 | 0.02 | 0.02 |

TABLE 4-continued

Compositions Prepared for Patch Test (Skin Irritation)

|  | 1 | 2 | 3 | 4 | 5 | 6 |
|---|---|---|---|---|---|---|
| ACID |  |  |  |  |  |  |
| Steareth-2 |  | 1.70 |  |  |  |  |
| Polysorbate-21 |  | 1.70 | 0.10 | 0.15 | 0.20 | 0.15 |
| Laureth-3 |  |  | 0.90 | 1.35 | 1.80 | 1.35 |
|  | 100.00 | 100.00 | 100.00 | 100.00 | 100.00 | 100.00 |
| TOTAL SURFACTANT--> | 0.00 | 3.40 | 1.00 | 1.50 | 2.00 | 1.50 |
| Avg. Erythema Score | 0.78 | 1.50 | 0.61 | 0.67 | 0.67 | 0.61 |

Skin Irritation was evaluated on 9 subjects who were tested using the closed patch (Hilltop Chamber). The subjects wore the patches for 48 hours. Skin irritation (erythema) was graded 3 hours after removal of patches
CONCLUSION: There was no significant difference in irritation between samples 1,3,4,5 & 6. Sample 2 was judged to be more irritating than the other samples The inventive skin-conditioning composition has been described both generically, and with reference to specific embodiments. Variations will occur as understood by those of ordinary skill in the art, without the exercise of inventive faculty, and remain within the scope of the invention, save as limited by the recitation of the claims presented below. In particular, ester identities, oil selections, and combinations of oil, ester-and surfactant may be modified within the guidelines provided, and arrive at suitable formulas. Additionally, the amount of residue left behind after rinsing may be slightly more or less than that set forth specifically, under situations requiring special consideration. These remain within the spirit and body of the invention.

what is claimed as new and is desired to be secured by Letters Patent of the United States is:

1. A rinse-off skin-conditioning composition for application to human skin while showering, comprising:
   (a) 49–98 percent by weight of the total composition of a mineral oil,
   (b) 0.5–5 percent by weight of the total composition of a mixture of di-block copolymers and tri-block copolymers, wherein said copolymers are comprised of (A) styrene and (B) at least one monomer selected from the group consisting of isoprene, ethylene, propylene, butylene and butadiene,
   (c) 0–40 percent by weight of the total composition of a fatty acid ester emollient, and
   (d) 1–4 percent by weight of a non-ionic surfactant, an anionic surfactant or mixture thereof, soluble in the combination of (a), (b) and (c) and effective in dispersing the composition into water such that upon rinsing said composition from said skin, approximately 3–25 percent by weight of the composition remains on the skin as residue.

2. The composition of claim 1, wherein said surfactant is selected from the group consisting of Laureth-3, Laureth-4, Oleth-3, Isosteareth-2, Trideceth-3, C9-11 Pareth-3, C9-11 pareth-6, C11-15 Pareth-3, C12-13 Pareth-3, C11-15 Pareth-5, PEG-40 Sorbitan Peroleate, PEG-40 Sorbitan Hexaoleate, PEG-50 Sorbitan Hexaoleate, Steareth-2, Laureth-3 Phospate, Cocoamide MEA, Lauramide MEA, Mystiramide MEA, Polysorbate-21, dioctyl sodium sulfosuccinate, dihexyl sodium sulfosuccinate, dinonyl sodium sulfosuccinate, ditridecyl sodium sulfosuccinate, propylene glycol isoceteth-3 acetate, propylene glycol ceteth-3 acetate, and mixtures thereof.

3. The composition of claim 1, wherein said surfactant is selected from the group consisting of:
   1) ethoxylated long chain alcohols of the formula $CH_3(CH_2)_xO(OCH_2CH_2)_yOH$ 2) ethoxylated sorbitan esters;
   3) sodium dialkyl sulfosuccinates
   4) phosphoric acid esters of ethoxylated long chain alcohols of the formula $CH_3(CH_2)_xO(OCH_2CH_3)_yOPO_3H$ 5) monoethanol amides of long chain alcohols of the formula $CH_3(CH_2)_xCONHCHCH_2OH$ 6) acetic acid esters of ethoxylated propylene glycol ethers of long chain alcohol and mixtures of 1–6 wherein X is an integer of about 8–22 and y is an integer of about 2–6.

4. The composition of claim 1, wherein said surfactant is a mixture of anionic and nonionic surfactants.

5. The composition of claim 1, wherein said surfactant is selected such that when said composition is mixed with an amount of water equal or greater than the composition and shaken, a white, milky emulsion is produced.

6. The composition of claim 1, wherein said copolymer is a mixture of di-block and tri-block copolymers comprised of styrenic monomer for a hard segment and monomers selected from the group consisting of ethylene, propylene, butylene, butadiene and isoprene for a soft segment.

7. The composition of claim 1, wherein said ester is a fatty acid ester of a monohydric alcohol, a fatty acid ester of an ethoxylated monohydric alcohol, a di- or tri-fatty acid ester of a monohydric alcohol, a fatty acid ester of a polyhydric alcohol and mixtures thereof.

8. The composition of claim 1, wherein said composition further comprises at least one additive selected from the group consisting of a fragrance, a preservative, a colorant, and an antibiotic.

9. A method of applying a skin-conditioning composition to human skin in a method to effect skin conditioning, comprising:
   1) applying a rinse-off skin-conditioning composition for application to human skin while showering, comprising:
      (a) 49–98 percent by weight of the total composition of a mineral oil,
      (b) 0.5–5 percent by weight of the total composition of a mixture of di-block copolymers and tri-block copolymers, wherein said copolymers are comprised of (A) styrene and (B) at least one monomer selected from the group consisting of ethylene, propylene, butylene, isoprene and butadiene,
      (c) 0–40 percent by weight of the total composition of a fatty acid ester emollient, and
      d) 1–4 percent by weight of a non-ionic surfactant, an anionic surfactant or mixture thereof, soluble in the combination of (a), (b) and (c) and effective in dispersing the composition into water such that upon rinsing said composition from said skin, approximately 3–25 percent by weight of the composition remains on the skin as residue 2) rinsing said composition from said individuals skin in the process of showering, and
3) completing showering, such that, upon completion of showering, approximately 3–25 percent by weight of the composition applied remains on the individual's skin as a residue after showering.

* * * * *